United States Patent [19]
Keana et al.

[11] Patent Number: 5,580,697
[45] Date of Patent: Dec. 3, 1996

[54] CHEMICAL FUNCTIONALIZATION OF SURFACES

[75] Inventors: John F. W. Keana; Martin N. Wybourne; Sui X. Cai; Mingdi Yan, all of Eugene, Oreg.

[73] Assignee: State of Oregon Acting by and through the State Board of Higher Education on Behalf of the University of Oregon, Eugene, Oreg.

[21] Appl. No.: 267,851

[22] Filed: Jun. 23, 1994

Related U.S. Application Data

[63] Continuation of Ser. No. 6,453, Jan. 21, 1993, abandoned.

[51] Int. Cl.$^6$ ........................................................ G03C 5/00
[52] U.S. Cl. ................................................ 430/296; 430/942
[58] Field of Search ........................................ 430/296, 942

[56] References Cited

U.S. PATENT DOCUMENTS

| | | | |
|---|---|---|---|
| 3,205,206 | 9/1965 | Marcantonio | 260/88.2 |
| 3,211,713 | 10/1965 | Breslow | 260/93.7 |
| 3,284,421 | 11/1966 | Breslow | 260/80.5 |
| 3,888,833 | 6/1975 | Lednicer et al. | 260/79.3 R |
| 4,007,089 | 2/1977 | Smith, III | 195/68 |
| 4,309,453 | 1/1982 | Reiner et al. | 427/54.1 |
| 4,654,292 | 3/1987 | Oie et al. | 430/197 |
| 5,002,582 | 3/1991 | Guire et al. | 623/66 |
| 5,277,772 | 1/1994 | Harmer | 264/157.69 |
| 5,465,151 | 11/1995 | Wybourne et al. | 356/361 |

OTHER PUBLICATIONS

Osteraas et al., "Modification of Polythylene Sufaces with Carbethoxy Substituted Carbenes and Nitrenes," *J. Appl. Polym. Sci.* 13:1537–1544 (1969).

Osteraas et al., "Incorportaion of Functional Groups onto the Surface of Polyethylene," *Nature* 221:1140–1141 (1969).

Abbott et al., "Manipulation of the Wettability of Surfaces on the 0.1–to 1–Micrometer Scale Through Micormachining and Molecular Self–Assembly," *Science* 257:1380–1381 (1992).

Stenger et al., "Coplanar Molecular Assemblies of Amino–and Perfluorinated Alkylsilanes: Characterization and Geometric Definition of Mammalian Cell Adhesion and Growth," *J. Am. Chem. Soc.* 114:8435–8442 (1992).

Wring et al., "Chemically Modified, Carbon–based Electrodes and Their Application as Electrochemical Sensors for the Analysis of Biologically Important Compounds–A Review," *Analyst* 117:1215–1229 (1992).

Yokohama et al., "Synthesis of Poly(ethylene oxide) with Heterobifunctional Reactive Groups at Its Terminals by an Anionic Initiator," *Bioconjugate Chem.* 3:275–276 (1992).

Braybrook et al., "Organic Polymer Sufaces for Use in Medicine: Their Formation, Modification, Characterisation and Application," *Prog. Polym. Sci.* 15:715–734 (1990).

Carlsson et al., "Plasma Modification and Its Effect on Polymer–Polymer and Polymer–Metal Adhesion," *Polymer Materials Science and Engineering* (Fall Meeting 1992, Washington, D.C.) vol. 67, pp. 21–23 (1992).

Cai et al., "Introduction of Functional Groups into Polymer Films via Deep–UV Photolysis or Electron–Beam Lithography: Modification of Polystyrene and Poly(3–octylthiophene) by a Functionalized Perfluorophenyl Azide," *Chem. Mater.* 4:879–884 (1992).

*Primary Examiner*—Mark Chapman
*Attorney, Agent, or Firm*—Klarquist Sparkman Campbell Leigh & Whinston, LLP

[57] ABSTRACT

Methods for covalently modifying surfaces of various substrates are disclosed, along with various substrates having surfaces modified by such methods. Candidate surfaces include various polymeric, siliceous, metallic, allotrophic forms of carbon, and semiconductor surfaces. The surfaces are exposed to a reagent, having molecules each comprising a nitrenogenic group and a functionalizing group, in the presence of energized charged particles such as electrons and ions, photons, or heat, which transform the nitrenogenic reagent to a nitrene intermediate. The nitrene covalently reacts with any of various chemical groups present on the substrate surface, thereby effecting nitrene addition of the functionalizing groups to the substrate surface. The functionalizing groups can then participate in downstream chemistry whereby any of a large variety of functional groups, including biological molecules, can be covalently bonded to the surface, thereby dramatically altering the chemical behavior of the surface. Such functionalizations of the surface can be done in a single reactive step or in multiple reactive steps.

29 Claims, 7 Drawing Sheets

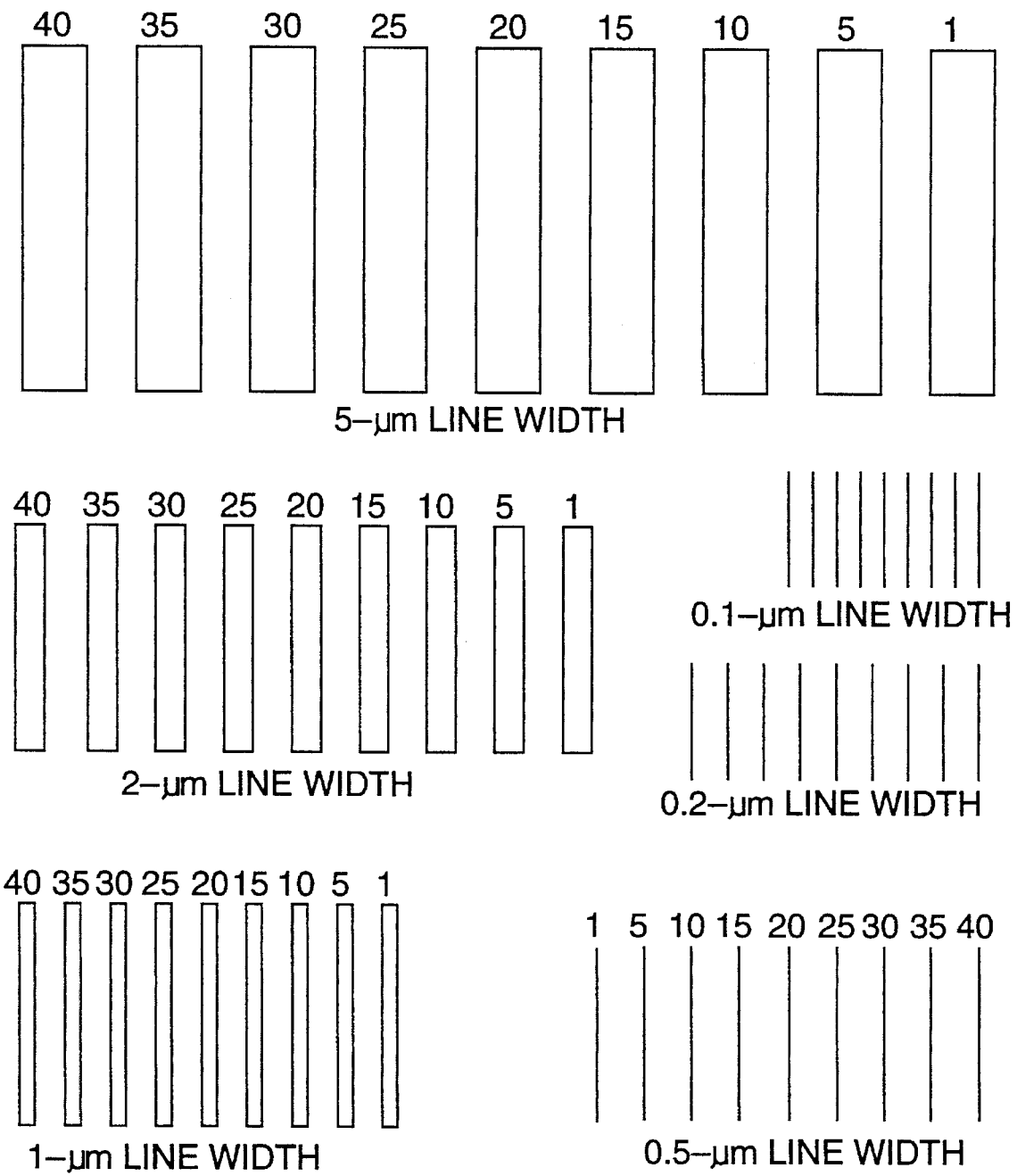

CHEMICAL FUNCTIONALIZATION OF SURFACES

This invention was made with U.S. government support under grant number GM 27137 from the National Institute of General Medical Sciences and grant number N00014-92-J-1412 (R&T code 413t011) from the Office of Naval Research. The U.S. government has certain rights in the invention.

This application is a continuation of application Ser. No. 08/006,453, filed on Jan. 21, 1993 now abandoned.

FIELD OF THE INVENTION

This invention pertains to chemical modification of surfaces, including surfaces of polymeric materials and other materials.

BACKGROUND OF THE INVENTION

Chemical modification of various surfaces has been the subject of intensive research. Examples of such surfaces include polymers, Braybrook et al., *Prog. Polym. Sci.* 15:715–734 (1990); metals, Stratmann, *Adv. Mater.* 2:191–195 (1990); silica, Bhatia et al., *J. Am. Chem. Soc.* 114:4432–4433 (1992); and graphite, Delamar, *J. Am. Chem. Soc.* 114:5883–5884 (1992). This research has been principally directed toward the development of novel composites, Baum et al., *Chem. Mater.* 3:714–720 (1991); resist materials, MacDonald et al., *Chem. Mater.* 3:435–442 (1991); biosensors, Pantano et al., *J. Am. Chem. Soc.* 113:1832–1833 (1991); and biomaterials, Allcock et al., *Chem. Mater.* 3:450–454 (1991). Recently, surface modification has been combined with photolithography to spatially direct the synthesis of peptides or oligonucleotides, Fodor et al., *Science* 251:767–773 (1991) and Kiederowski, *Angew. Chem. Int. Ed. Eng.* 30:822–823 (1991); and immobilization of biopolymers. Rozsnyai et al., *Angew. Chem. Int. Ed. Eng.* 31:759–761 (1992). Most of the surface modification processes known in the art involve sequential treatment of surfaces with chemical reagents. Id. Only a few such studies have involved the use of azides as surface-modification reagents. Breslow, in Scriven (ed.) *Azides and Nitrenes*, chapter 10, Academic Press, N.Y. (1984); Harmer, *Langmuir* 7:2010–2012 (1991).

Examples of existing methods for modifying polymer films include sulfonation of polystyrene, Gibson et al., *Macromolecules* 13:34 (1980); sulfonation of poly(aryloxy-)phosphazenes, Allcock et al., *Chem. Mater.* 3:1120 (1991); plasma treatment of polyester, Porta et al., *Chem. Mater.* 3:293 (1991); base hydrolysis of polyimide, Lee et al., *Macromolecules* 23:2097 (1990); base hydrolysis of polyphosphazenes, Allcock et al., *Chem. Mater.* 3:1441 (1991); and base treatment of poly(vinylidene fluoride), Dias et al., *Macromolecules* 17:2529 (1984).

Another conventional method for modifying polymers comprises exposing the surface of a hydrocarbon polymer such as polyethylene with nitrene or carbene intermediates generated in the gas phase. Breslow, in Scriven (ed.), *Azides and Nitrenes*, chapter 10, Academic Press, N.Y. (1984). Also, difluorocarbene generated in solution has been reported to modify 1,4-polybutadienes. Siddiqui et al., *Macromolecules* 19:595 (1986).

Perfluorophenyl azides (PFPAs) have been shown to exhibit improved CH-insertion efficiency over their non-fluorinated analogues when the PFPAs were photolyzed in hydrocarbon solvents such as cyclohexane or toluene. Keana et al., *Fluorine Chem.* 43:151 (1989); Keana et al., *J. Org. Chem.* 55:3640 (1990); Leyva et al., *J. Org. Chem.* 54:5938 (1989); and Soundararajan et al., *J. Org. Chem.* 55:2034 (1990). PFPAs were initially developed as efficient photolabeling reagents. Cai et al., *Bioconjugate Chem.* 2:38 (1991); Pinney et al., *J. Org. Chem.* 56:3125 (1991); and Crocker et al., *Bioconjugate Chem.* 1:419 (1990). Recently, bis-(PFPA)s have been shown to be efficient cross-linking agents for polystyrene, Cai et al., *Chem. Mater.* 2:631 (1990); and poly(3-octylthiophene), Cai et al., *J. Molec. Electron.* 7:63 (1991).

In view of the present state of the art in chemical modification of surfaces, there remains a need for other methods for chemically functionalizing molecules on the surfaces of various materials, particularly in a single step.

There is also an ongoing need for new types of chemically modified molecules, particularly functionalized polymers, for use in any of a wide variety of applications.

SUMMARY OF THE INVENTION

The foregoing needs are met by the present invention which provides methods for covalently modifying (i.e., functionalizing) the surfaces of various substrates, and provides various substrates having chemically modified surfaces.

Substrates that can be functionalized according to the present invention include, but are not limited to, a wide variety of polymeric substrates as well as various allotrophic forms of elemental carbon (e.g., graphite, "carbon electrodes," diamond and diamond films, and fullerenes such as $C_{60}$ and $C_{70}$), siliceous materials, and any of various metals. The substrate can also be a semiconductor material such as silicon, gallium arsenide, and other semiconducting materials (doped or not doped).

According to the present invention, substrate surfaces are functionalized by exposing the surface to a nitrenogenic functionalizing reagent in the presence of a reaction-energy source such as photons, electrons, or heat. In the presence of the reaction-energy source, the functionalizing reagent forms a nitrene intermediate that covalently reacts with —CH, —NH, —OH, —C=C—, —C—C— and other groups on the substrate surface so as to cause "nitrene addition" or "nitrene insertion" of the functionalizing reagent to the substrate surface.

In order to form nitrene intermediates, the functionalizing reagent used for reaction with the surface molecules must terminate with an azide group or analogous chemical group capable of forming a reactive nitrene when exposed to a reaction-energy source.

According to the present invention, the substrate surface is functionalized via either a single-stage or a multi-stage process. In a multi-stage process, each stage typically involves different functionalizing reagents. In both single- and multi-stage processes, at least one stage involves a nitrenogenic functionalizing reagent.

In a single-stage process, each molecule of the functionalizing agent comprises, in addition to the nitrenogenic group, a functionalizing group covalently coupled to the nitrenogenic group. The functionalizing group can be virtually any desired chemical group that does not cross-react with the nitrene intermediate or otherwise significantly interfere with the nitrene addition reaction of the functionalizing agent with the substrate surface. E.g., the functionalizing group can be selected from, but is not necessarily limited to, radioactive labels, fluorescent labels, enzymes, pharmacologically active groups, diagnostically active groups, antibodies, nucleic acids, surfactants, and any of a wide variety of other groups.

Functionalizing reagents adapted to functionalize substrates in multi-stage reactions can be configured in several ways. According to one method, a first functionalizing reagent is reacted with the substrate so as to achieve covalent attachment of the first functionalizing-reagent molecules to the substrate surface; afterward, a second functionalizing reagent is added so as to react with, and therefore covalently bond to, the attached first functionalizing-reagent molecules. In such a method, the first functionalizing reagent comprises molecules each comprising, in addition to the nitrenogenic group, a first functionalizing group adapted to participate in downstream chemistry after the first functionalizing reagent has been covalently bonded to the substrate surface via nitrene addition. For example, the first functionalizing group can be an active ester that is reactive with —NH groups, —OH groups, or other nucleophilic groups on molecules of a second functionalizing reagent. The second functionalizing reagent, then, can provide a second functionalizing group ultimately desired to be attached to the substrate surface, such as an enzyme, antibody, diagnostic agent, or therapeutic agent.

An alternative multi-stage process comprises first reacting the second functionalizing reagent (comprising the second, or ultimately desired, functionalizing group) with the first functionalizing reagent (including a nitrenogenic group); then, in a second reaction, reacting the product of the first reaction with the substrate in the presence of a reaction-energy source so as to covalently attach the product of the first reaction to the substrate surface via nitrene addition.

A class of preferred functionalizing reagents for single- and multi-stage processes according to the present invention consists of N-hydroxysuccinimide active ester-functionalized perfluorophenyl azides (NHS-PFPAs). The NHS active ester groups become covalently attached to the substrate surface via generation during the reaction of highly reactive nitrene intermediates derived from the PFPA portion of the reagent molecules. (The reactive nitrene portion of the intermediates are preferably constrained structurally such that the nitrene portion cannot react intramolecularly with the NHS active ester portion.) Thus, the substrate surface becomes "modified" (i e., "functionalized"). Afterward, the active esters can participate in further reactions with a variety of reagents containing primary amines or hydroxyls (such as biomolecules) by way of amide or ester formation, respectively.

According to another aspect of the present invention, a nitrene-forming functionalizing reagent can be applied, such as in the form of a film, to the substrate surface. Then, the coated surface is exposed to a reaction-energy source (such as photons or a beam of particles such as an electron beam) in a spatially selective way to functionalize certain regions of the surface and not others, thereby creating a functionalized pattern on the surface. Such patterns can have dimensions measured in micrometers and smaller, due to the highly resolved manner in which the coated surface can be exposed to the reaction-energy source. Thus, the present invention has wide applicability in microelectronics and in the construction of novel micron-scale biosensors.

BRIEF DESCRIPTION OF THE DRAWINGS

FIG. 4B is a legend for FIG. 4A showing beam dosages and linewidths.

DETAILED DESCRIPTION

Figure 1:
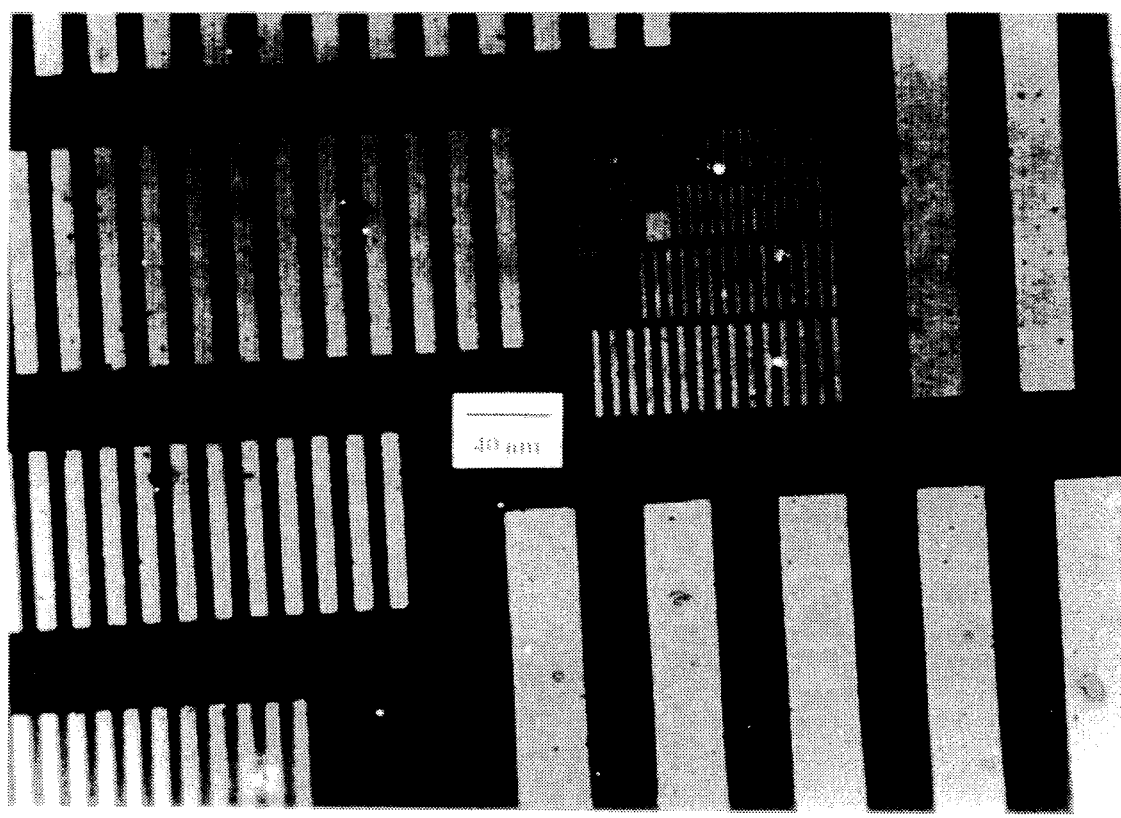
FIG. 1 is a photograph of micron-sized patterns as observed under a fluorescence microscope (450–490 nm excitation wavelength; >510 nm emission) showing the surface modification of a polystyrene film as described in Example 4.

The following terms are used herein:

A "substrate" is a non-fluid material providing a surface that can be functionalized according to the present invention. A substrate can comprise molecules (e.g., thermoplastic polymer molecules), a thermoset molecular network (e.g., cross-linked polymer molecules), or other atomic or molecular association such as found in certain glasses and crystals.

A "surface molecule" is a substrate molecule having at least a portion thereof present on the substrate surface.

A "polymeric substrate" is a substrate comprising polymer molecules or a network of polymer molecules.

A "polymer molecule" is a large molecule formed by the covalent linking together of smaller molecules termed "monomers." The monomers present in a polymer molecule can be the same or different. Polymer molecules can be natural, such as (but not limited to) cellulose, starch, proteins, and nucleic acids; or synthetic such as (but not limited to) nylon and polyethylene. In a substrate, polymer molecules can be associated with each other in any of several ways, including non-covalently (as a thermoplastic) or a covalently cross-linked network (as a thermoset).

A "functionalized substrate" is a substrate to which one or more functional groups are covalently bonded according to the present invention.

A "functional group" is a group of one or more atoms bonded together in an organized way so as to have a desired chemical property. According to the present invention, functionalizing reagents functional group can, when covalently bonded to a substrate surface according to the present invention, participate in one or more additional bonding reactions with either a similar functional group or a different type of functional group. Such bonding reactions can result in: (a) attachment to the functional groups of any of a variety of additional functional groups; or (b) coupling together (cross-linking) of the functionalized substrate molecules.

The term "functionalized polymer" can pertain to either a functionalized polymeric substrate or a functionalized polymer molecule. A "functionalizing reagent" according to the present invention is a reagent adapted for functionalizing a substrate according to the present invention. Molecules of functionalizing agents have at least one nitrenogenic group (as a first functional group) coupled to a second functional group, wherein the nitrenogenic group is preferably constrained by the functionalizing-reagent molecular structure between the nitrenogenic group and the functional group. The nitrenogenic groups are capable under reaction conditions of functionalizing a substrate surface.

A "nitrenogenic group" on a functionalizing reagent is a chemical moiety that, when exposed to a reaction-energy source, becomes a nitrene group.

A "nitrene group" (also generally termed "nitrene" or "nitrene intermediate") is a particular form of nitrogen group that can be depicted as a singlet by the structure: R-$\bar{\text{N}}$, and as a triplet by the structure: R- $\bar{\text{N}}\cdot$. Nitrenes are regarded by persons skilled in the art as the nitrogen analogs of carbenes. Like carbenes, nitrenes are generally regarded as intermediates. Nitrenes are highly reactive and generally cannot be isolated under ordinary conditions. However, certain chemical reactions such as reactions according to the present invention would not otherwise be explainable by known reaction mechanisms without the presumed existence of nitrenes. Important nitrene reactions can be summarized by the following:

(a) Nitrenes, including aryl nitrenes, can undergo addition reactions at —CH sites and at —NH sites; e.g.:

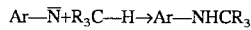

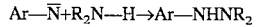

(b) Nitrenes can also undergo addition at —C—C— and —C=C— bonds; e.g.:

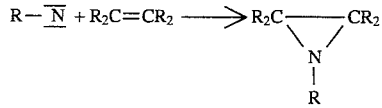

As used herein, the term "addition reaction" when used in the context of reactions of the nitrene group of the functionalizing reagent with surface molecules, generally refers to any of the various addition and insertion reactions that nitrenes can undergo with molecules on the substrate surface according to the present invention.

According to the present invention, a functionalizing reaction occurs when a functionalizing reagent comprising a nitrenogenic group is exposed to a reaction-energy source, which converts the nitrenogenic group to a nitrene intermediate. The functionalizing reaction proceeds by reaction of the nitrene intermediate with the substrate surface.

A "reaction-energy source" is an energy source that drives a functionalizing reaction according to the present invention by, in particular, converting nitrenogenic groups on functionalizing reagent molecules to nitrenes which react with the substrate surface. Suitable reaction-energy sources include (but are not limited to): photons (such as ultraviolet (UV) light, deep-UV light, laser light, X-rays, and heat in the form of infrared radiation or conductive heating), energized electrons (such as an electron beam), and energized ions (such as an ion beam). These reaction-energy sources are conventionally used for such tasks as lithography, scanning microscopy, and, in the case of UV and visible photons, effecting photochemical reactions and excitation of fluorescent molecules.

A "functionalizing reaction" is a reaction in which a substrate surface is functionalized according to the present invention. A functionalizing reaction can consist of one or more stages. At least one stage involves the reaction in the presence of a reaction-energy source of the substrate surface with molecules of a functionalizing reagent comprising nitrenogenic groups.

According to the present invention, a substrate surface is functionalized by a chemistry whereby functional groups on functionalizing reagent molecules become covalently bonded to the surface. Such covalent bonding is achieved by conversion of nitrenogenic groups on the functionalizing reagent molecules (the functionalizing reagent molecules also each comprising a desired functional group as set forth below) to a nitrene intermediate highly reactive with the substrate surface by exposure of the functionalizing reagent molecules to a reaction-energy source.

The functionalizing reagent is preferably selected from a group consisting generally of: aryl azides, alkyl azides, alkenyl azides, alkynyl azides, acyl azides, and azidoacetyl derivatives, all capable of carrying a variety of substituents. Most preferably, fluorine (and/or chlorine) atoms are present to the maximum extent possible in the positions on the functionalizing reagent molecule adjacent the azide group.

Each of the foregoing azides may also contain within the same molecule any of the following functional groups, constrained structurally from reacting with the nitrene moiety after the nitrene moiety is generated:

(a) carboxyl groups and various derivatives thereof such as (but not necessarily limited to): N-hydroxysuccinimide esters; N-hydroxybenztriazole esters; acid halides corresponding to the carboxyl group; acyl imidazoles; thioesters; p-nitrophenyl esters; alkyl, alkenyl, alkynyl and aromatic esters, including esters of biologically active (and optically active) alcohols such as cholesterol and glucose; various amide derivatives such as amides derived from ammonia, primary, and secondary amines and including biologically active (and optically active) amines such as epinephrine, dopa, enzymes, antibodies, and fluorescent molecules;

(b) alcohol groups, either free or esterified to a suitable carboxylic acid which could be, for example, a fatty acid, asteroid acid, or a drug such as naprosin or aspirin;

(c) haloalkyl groups wherein the halide can be later displaced with a nucleophilic group such as a carboxylate anion, thiol anion, carbanion, or alkoxide ion, thereby resulting in the covalent attachment of a new group at the site of the halogen atom;

(d) maleimido groups or other dienophilic groups such that the group may serve as a dienophile in a Diels-Alder cycloaddition reaction with a 1,3-diene-containing molecule such as, for example, an ergosterol;

(e) aldehyde or ketone groups such that subsequent derivatization is possible via formation of well-known carbonyl derivatives such as hydrazones, semicarbazones, or oximes, or via such mechanisms as Grignard addition or alkyllithium addition; and (f) sulfonyl halide groups for subsequent reactions with amines, for example, to form sulfonamides.

A general reaction by which a functionalizing reagent is converted to a nitrene intermediate is:

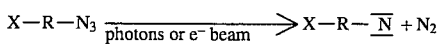

where X is the functional group and R is an aromatic ring, heteroaromatic ring, or other carbon-containing fragment.

A reaction-energy source comprising UV light can be supplied to the reaction by, for example, one of the following representative procedures: (a) The sample is placed in a well of a Rayonet Photochemical Reactor fitted with either 350-nm, 300-nm, or 254-nm lamps and irradiated at ambient temperature for several minutes under air. The duration of the irradiation can be adjusted to change the exposure dose. (b) The sample is irradiated through a high-resolution photomask, for example, by (but not limited to) projection UV lithography. (c) Photolysis is carried out in a KSM Karl Suss deep-UV contact aligner using a contact high-resolution photomask. It will be readily appreciated by persons skilled in the art that such procedures can also be generally used to provide the functionalizing reaction with photons of wavelengths other than UV.

A reaction-energy source comprising electrons can be supplied to the reaction by the following representative procedure: The sample is irradiated under vacuum by an electron or particle beam with an energy selected within the range 1–40 kV. (A representative electron-beam source is a JOEL 840A electron microscope modified for electron-beam lithography.) The beam is stepped across the surface of the treated substrate to expose certain areas and not others. A dwell time at each step can be adjusted to change the exposure dose.

Particularly effective functionalizing reagents are selected from the group of perfluorophenyl azides (PFPAs) derived from 4-azido-2,3,5,6-tetrafluorobenzoic acid in which the carbonyl group is further activated through reactive ester, amide, acid halide, or mixed anhydride formation.

For example, and not intended to be limiting, representative functionalized perfluorophenyl azides have the general structure:

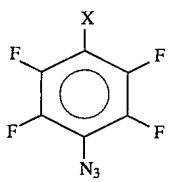

wherein X can be any of the following: CN, $CONH_2$, CHO, $CO_2Me$, COMe, $NO_2$, $CO_2H$, COCl, CO-Imidazole, CONHS, $CH_2OH$, $CH_2NH_2$, $COCH_2Br$, N-maleimido, NH-biotinyl, CONH-R (where R is a polypeptide moiety), CONH—X—S—S—Y—NH-biotinyl (where X and Y are spacer atoms and the S—S bond is reductively cleavable at a later stage), and CONHS—$SO_3Na$.

Representative activated PFPAs include (but are not limited to) the N-hydroxysuccinimide (NHS) ester A (also designated "NHS-PFPA"), the p-nitrophenyl ester B, the 1-hydroxybenzotriazole ester C, the acyl imidazole D, the acid chloride E, the mixed anhydride Y and the 2,2,2-trichloroethyl ester G:

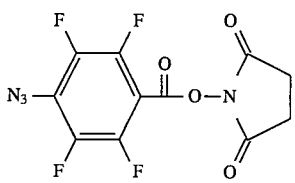 A

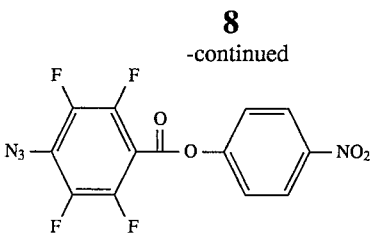 B

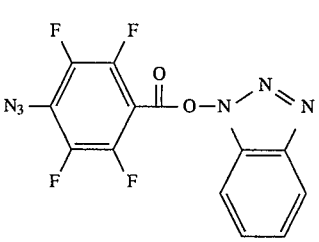 C

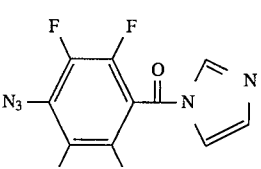 D

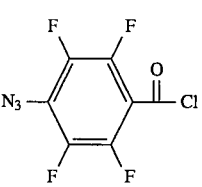 E

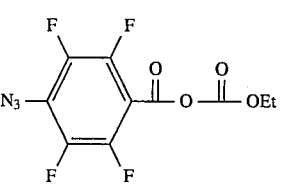 F

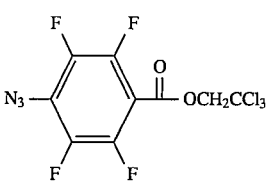 G

In addition to the foregoing candidate functionalizing reagents, it is possible to utilize other PFPAs having "spacers" situated between the reactive functional group and the PFPA moiety, such as:

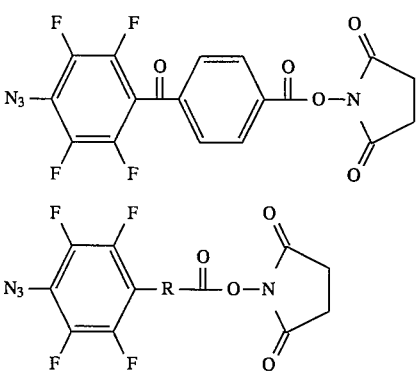

Other candidate aryl azides useful as functionalizing reagents are similar to the above examples except that another aryl moiety replaces the PFPA, such as:

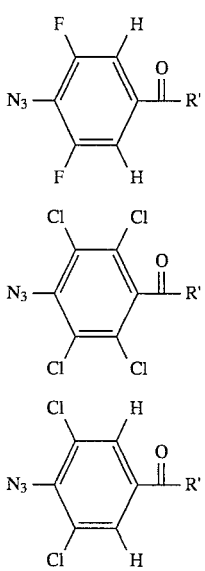

Candidate substrates that can be functionalized according to the present invention include, but are not limited to: polymeric substrates, graphite, metals, and siliceous materials; as well as silicon, gallium arsenide, and other semi-conducting materials.

In the case of siliceous substrates (e.g., glass, silica, mica, quartz) it is believed that the functionalizing reagents, when converted to corresponding nitrenes, react with SiO—H groups, Si—OH groups, or Si—OSi groups on the substrate surface.

In the case of graphite and other allotrophic forms of elemental carbon, it is believed that the functionalizing reagents, when converted to the corresponding nitrenes, react with carbon rings on the substrate surface.

Polymeric substrates that can be functionalized according to the present invention include virtually any polymeric material comprising polymer molecules possessing —CH groups, and/or —NH groups, and/or —OH groups and/or —C═C— sites. Such polymeric substrates include, but are not limited to:

(a) saturated polyolefins as exemplified by polyethylene, polyvinyl chloride, polytetrafluoroethylene, polypropylene, polybutenes, and copolymers thereof;

(b) acrylic resins such as polymers and copolymers of acrylic acid, methacrylic acid [poly(methylmethacrylate), poly(hexylmethacrylate)], and acrylonitrile;

(c) polystyrene and its analogues such as poly(p-chlorostyrene) and poly(p-hydroxystyrene);

(d) unsaturated polyolefins such as poly(isoprene) and poly(butadiene);

(e) polyimides such as polyimide(benzophenone tetracarboxylic dianhydride/tetraethylmethylenedianiline);

(f) polyesters such as poly(trimethylene adipate) and poly(hexymethylene sebacate);

(g) conjugated and conducting polymers such as poly(3-alkylthiophene), poly(3-alkylpyrrole), and polyaniline;

(h) inorganic polymers such as poly(aryloxyphosphazene), poly[bis(trifluoroethoxy)phosphazene], polysilanes, and polycarbosilanes, siloxane polymers, and other silicon-containing polymers;

(i) organic metals (i.e., organic polymers with metallic properties) such as polycroconaines and polysquaraines, as described in *Chemical and Engineering News* (Aug. 31, 1992), p.8.

(j) organometallic polymers such as palladium poly-yne and ferrocene-containing polyamides; and (k) polysaccharides such as cellulose fibers, chitin, and starch.

Functionalization of a substrate surface can occur in one or more stages, depending upon which functional group(s) are to be attached to the surface; whether or not it is necessary to protect the functional groups from undesired reactions during attachment to the surface; and on matters of convenience.

For example, in a two-stage functionalization protocol, each stage involves a different functionalizing reagent. The first stage involves a first functionalizing reagent such as a NHS-PFPA, which is converted during the course of the first-stage reaction to a nitrene intermediate. During the first stage using, for example, a polymeric substrate, the NHS active-ester groups on the NHS-PFPA molecules become covalently attached to surface polymer molecules by a reaction that can be generally indicated as follows shown in Scheme 1:

Scheme 1

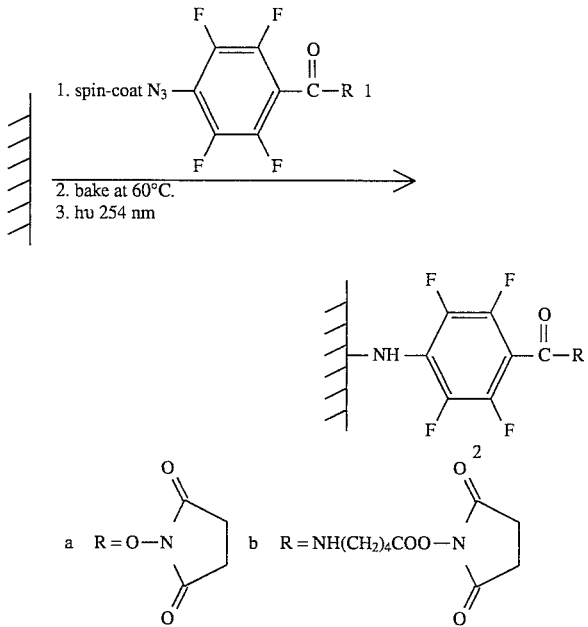

Thus, this first-stage reaction requires generation of a highly reactive nitrene intermediate derived from the NHS-PFPA 1 by exposure of the NHS-PFPA to a reaction-energy source.

As can be seen, the NHS-ester portions of the PFPAs do not participate in this first-stage chemistry. Rather, the NHS-esters, after being transferred to the surface molecules, are utilized in second-stage chemistry, discussed below.

In the second stage, the NHS esters readily react with molecules of a second functionalizing reagent. The second functionalizing reagent is selected from a group consisting of molecules possessing primary or secondary amines and/or hydroxyls. Reaction of NHS-esters with primary amines proceeds via amide formation as shown in Scheme 2:

Scheme 2

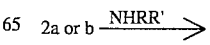

-continued

Scheme 2

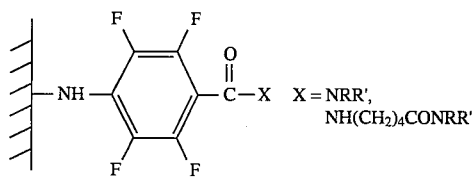

wherein compounds 2a and 2b are as shown in Scheme 1. Reaction of NHS-esters with hydroxyls proceeds via ester formation, as shown in Scheme 3:

Scheme 3

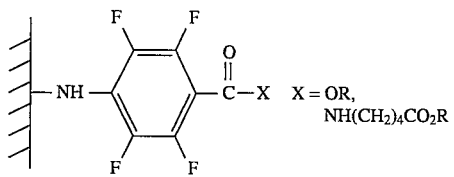

wherein compounds 2a and 2b are as shown in Scheme 1.

Since many types of biological molecules possess amine and/or hydroxyl groups, these molecules can serve as functionalizing reagents adapted for reaction in a second-stage functionalization reaction with HNS-esters covalently bonded to the surface molecules in a first-stage functionalization reaction. Thus, it is possible to attach any of a wide variety of molecules, including macromolecules such as proteins, nucleic acids, carbohydrates, and various other molecules, to substrates using methods according to the present invention.

It is also possible according to the present invention to first prepare nitrenogenic derivatives of molecules (such as biomolecules, drugs, analytes, catalysts [including transition metals], and diagnostic agents) to be attached to the substrate, apply the derivatives to a surface of the substrate, then expose the treated surface to a reaction-energy source to cause the nitrenogenic derivatives to covalently bond to surface molecules via nitrene intermediates. It is necessary for the nitrenogenic moiety to be structurally constrained such that the nitrene cannot readily react with another part of the same molecule. Thus, the 4-position of the phenyl ring is the preferred position for the azide group.

To convey the scope of the present invention without intending in any way to be limiting, the following representative functionalizations according to the present invention are provided:

(a) Carcinogenic or mutagenic polycyclic aromatic hydrocarbons can be attached to a substrate to create a "carcinogenic" surface. Candidate polycyclic hydrocarbons include ethidium compounds and various pyrene compounds (such as 1-pyrenemethylamine and 6-aminochrysene). It is also possible, when attaching such compounds to a substrate, to employ "spacer groups" serving to "lift" the hydrocarbon from the substrate surface. A representative spacer-containing hydrocarbon is the primary amine derived from 1-pyrenebutyric acid. Such reactions can be depicted generally as shown in Scheme 4:

Scheme 4

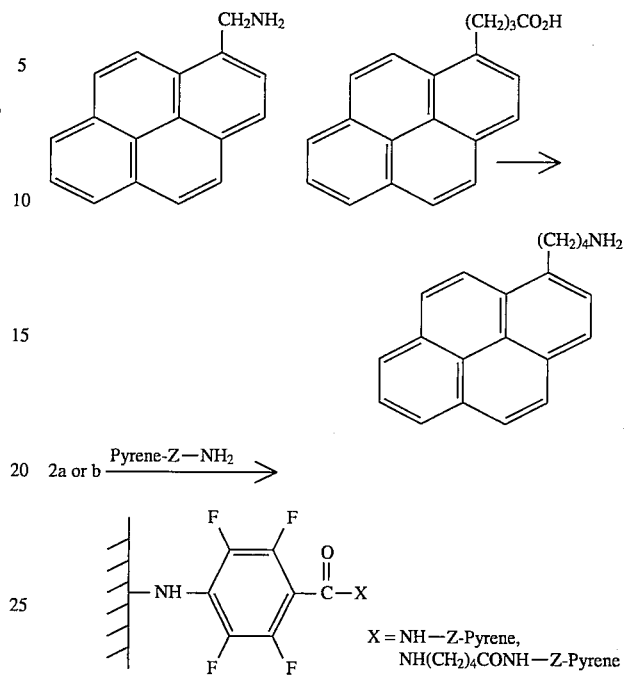

wherein 2a and 2b are as shown in Scheme 1 and Z represents a spacer group.

(b) The hydrophobicity of a substrate surface can be altered, after attachment of NHS-ester groups to the substrate surface in a first-stage reaction (via a nitrene Intermediate), by reaction of the NHS-ester groups with long-chain aliphatic amines such as 1-aminohexadecane in a second-stage reaction. Such a reaction can be generally depicted as shown in Scheme 5:

Scheme 5

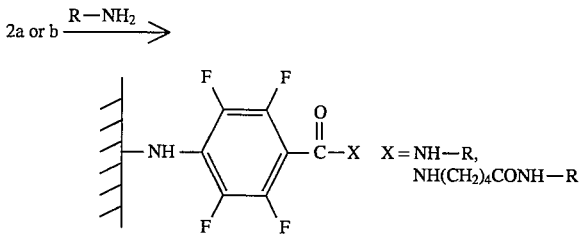

wherein R is a chain of hydrophobic atoms such as, for example, $C_{22}H_{25}$—, oleyl, octadecyl, 3-β-aminocholestane, or hexyldimethylsilyl; and 2a and 2b are as shown in Scheme 1.

(c) The hydrophilicity of the substrate surface can be altered, after attachment of NHS-ester groups to the substrate surface in a first-stage reaction (via a nitrene intermediate), by reaction of the NHS-ester groups with amine-possessing highly polar molecules in a second-stage reaction. Such amine-possessing polar molecules include (but are not necessarily limited to): glucosamine, ethanolamine, polyethyleneimine (protonated at pH 7), polylysine (also protonated at pH 7), glycerol, and other polyhydroxy compounds. Such reactions can be generally depicted as shown in Scheme 5 but wherein R is $HOCH_2CH_2$—, or $NH_2(CH_2CH_2NH$—$)_n$—$CH_2CH_2$—; and 2a and 2b are as shown in Scheme 1. For polyalcohols, such reactions can be generally depicted as shown in Scheme 6:

Scheme 6

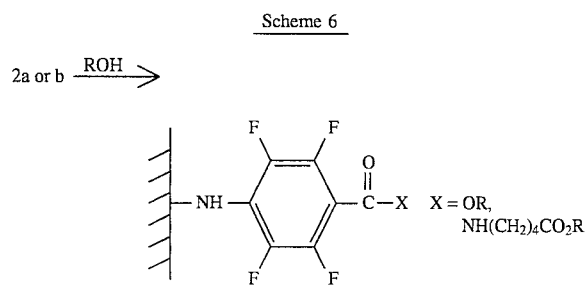

wherein R is, for example, CH—CHOH—CH$_2$OH; and 2a and 2b are as shown in Scheme 1.

(d) The substrate surface can be made surface-active in regions where NHS-ester groups have already been attached to the substrate surface in a first-stage reaction. The reaction to make surface-active proceeds by a second-stage reaction employing any of various aminated or hydroxylated "detergent" molecules such as, for example, 1-amino-dodecanoic acid. At pH 7 and after attachment of this compound to the substrate, the carboxyl group is ionized and the compound extends away from the substrate surface as a long hydrophobic tail terminating in a polar carboxylate anion. Such reactions can be generally depicted as shown in Scheme 7:

Scheme 7

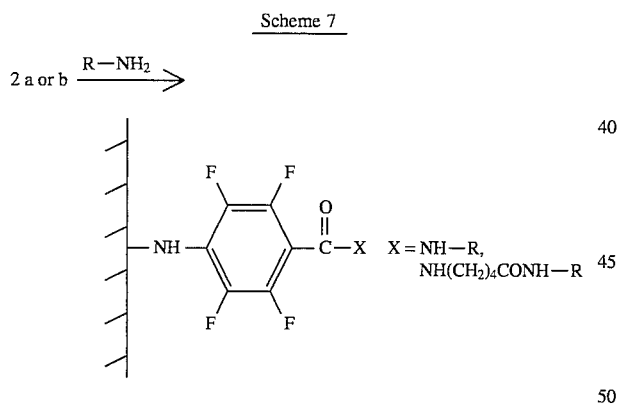

wherein R is —(CH$_2$)$_n$—CO$_2$H; and 2a and 2b are as shown in Scheme 1.

(e) Enzymes can be attached to a substrate surface functionalized in a first-stage reaction with, for example, an NHS active ester, by a second-stage reaction of, for example, a lysine amino group present on the enzyme molecules with the NHS active ester. A representative reaction is depicted as shown in Scheme 8:

Scheme 8

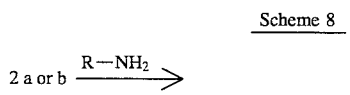

-continued
Scheme 8

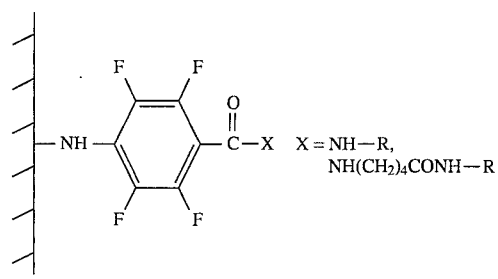

wherein R—NH$_2$ represents a lysine residue on a polypeptide such as an enzyme (e.g., horseradish peroxidase), lectin, or antibody; and 2a and 2b are as shown in Scheme 1.

(f) Antibodies, lectins, and other proteins can also be attached to substrates by functionalizing reactions similar to such reactions for attaching enzymes. Such attached molecules can then be used, for example, as highly selective sensing agents in biosensors.

(g) Specialized molecules can be attached to a substrate surface to control the wettability of the substrate surface or alter the ability of living cells to adhere to the substrate surface.

(h) Substrate surfaces can be biotinylated in a one or two-stage reaction, followed by treatment of the biotinylated surface with, for example, a derivatized avidin or streptavidin. The avidin or streptavidin are thus used as bridging units for subsequent attachment of other biomolecules to the surface. Representative reactions are as follows:

Scheme 9
Two-stage reaction

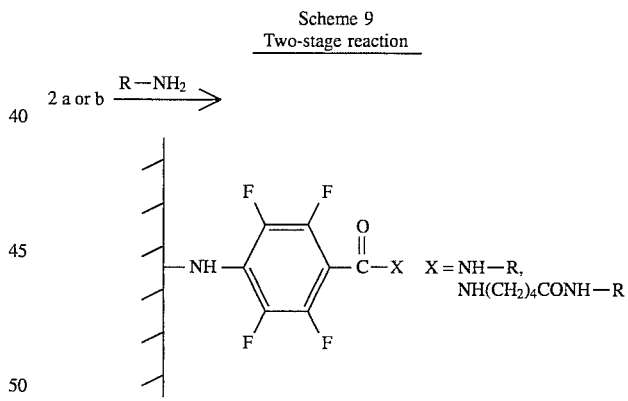

wherein 2a and 2b are as shown in Scheme 1 and RNH$_2$ represents the amino group of N-biotinylhexylenediamine:

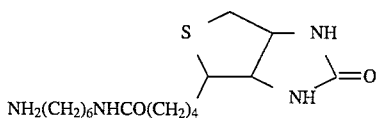

A one-stage reaction is exemplified by coating the substrate with the PFPA derivatives of biotin (see Scheme 12, compound 5), followed by exposure to photolysis or an electron beam.

To further illustrate and describe the present invention, the following examples are provided:

EXAMPLE 1

In this Example, we modified the surface of a representative polymer (polystyrene) using N-hydroxysuccinimide-functionalized (NHS-functionalized) perfluorophenyl azides (PFPAs) 1a and 1b (Scheme 10).

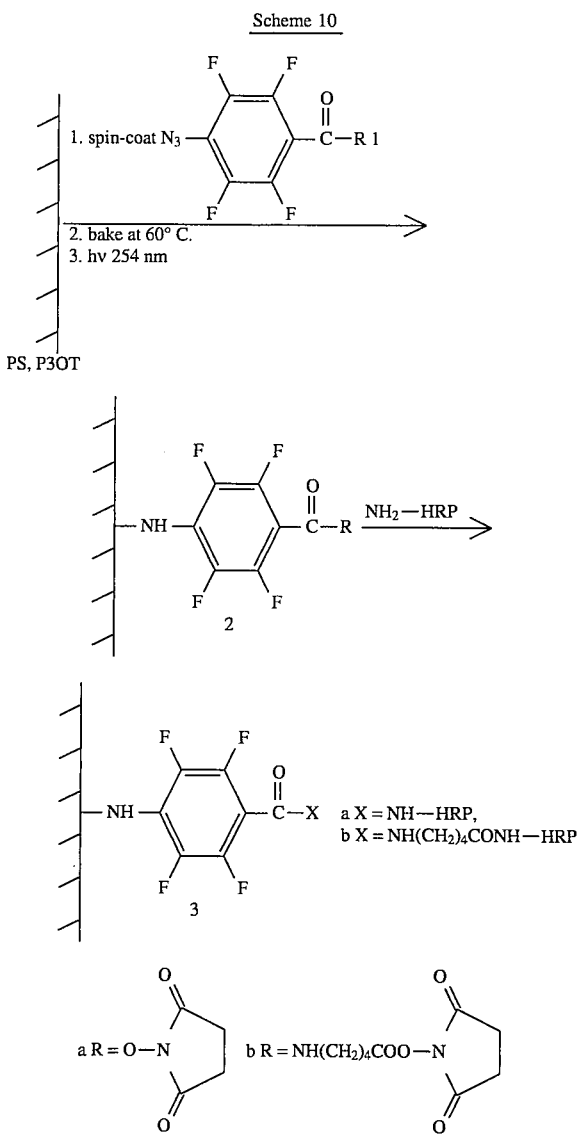

PFPA 1a is described in Keana et al., *J. Org. Chem.* 55:3640–3647 (1990).

PFPA 1b was prepared by N-acylation of 5-aminopentanoic acid with 4-azido-2,3,5,6-tetrafluorobenzamido) pentanoic acid (melting point (mp): 160°–161° C.; High-resolution mass spectrometry (HRMS) calculated for $C_{12}H_{10}F_4N_4O_3$: 334.0687; found m/z: 334.0710) which was then coupled with NHS in the presence of dicyclohexylcarbodiimide to yield N-succinimidyl 5-(4-azido-2,3,5,6-tetrafluorobenzamido)pentanoate 1b (mp: 93°–95° C.; HRMS calculated for $C_{16}H_{13}F_4N_5O_5$: 431.0850; found m/z: 431.0866).

A glass disc was spin-coated with a solution of 5 wt % polystyrene (PS) in xylene to form a film on the disk about 0.5 μm thick, as described in Cai et al., *Chem. Mater.* 4:879–884 (1992). The PS film was then spin-coated with a solution of 0.5 wt % of 1a or 1b in nitromethane and baked at 60° C. for 20 minutes. The baking step removed residual solvent and likely facilitated the diffusion of surface-deposited PFPAs into the PS films.

Subsequent photolysis of the film resulted in complete decomposition of the azido groups as indicated by FTIR (Fourier-Transform Infrared) spectroscopy. Photolysis was carried out in a Rayonet photoreactor with 254-nm lamps for 5 minutes at ambient temperature under air. FTIR was performed with a control sample using a NaCl disc as the support. Covalent attachment of the NHS PFPA esters to the PS surface yielded 2a and 2b (Scheme 10), respectively. We believe that the reaction occurred via C—H bond insertion of the highly reactive nitrene intermediate derived from 1a or 1b. See, Keana et al., *J. Org. Chem.* 55:3640–3647 (1990); Leyva et al., *J. Org. Chem.* 54:5938–5945 (1989); and Poe et al., *J. Am. Chem. Soc.* 114:5054–5067 (1992).

Since NHS active esters react readily with primary and secondary amines to form amides, Anderson et al., *J. Am. Chem. Soc.* 86:1839–1842 (1964), a variety of primary and secondary amine-containing reagents including biomolecules may in principle be attached to the polymer surface by this method.

EXAMPLE 2

In this Example, we immobilized horseradish peroxidase (HRP, Sigma) on PS films modified by PFPA-NHS as described in Example 1. Compounds are shown in Scheme 10.

The films 2a and 2b were incubated in a 50 -μM solution of HRP in $NaHCO_3$ buffer (pH 8.2) at 25° C. for 3 hours, Brinkley, *Bioconjugate Chem.* 3:2–13 (1992), followed by a thorough rinsing with phosphate buffer (pH 7.0). The enzyme activity of the resulting immobilized HRP films 3a and 3b was determined spectrophotometrically at 420 nm and 25° C. in phosphate buffer according using 2,2'-azino-bis(3-ethylbenzthiazoline-6-sulfonic acid) diammonium salt (ABTS) and hydrogen peroxide (1.8 mM ABTS/0.8 mM $H_2O_2$). Groome, *J. Clin. Chem. Clin. Biochem.* 18:345–349 (1980). Making the reasonable assumption that the immobilized HRP has the same activity as the native HRP, Nakane et al., *J. Histochem. Cytochem.* 22:1084–1091 (1974), the extent of immobilization of HRP was calculated to be 0.5±0.1 $ng/mm^2$ for 3a and 1.0±0.2 $ng/mm^2$ for the spacer-containing analogue 3b, indicating reasonable immobilization efficiencies.

An HRP molecule has a molecular weight around 40,000 daltons and a radius of 2.67 nm in the hydrated state. Steiner et al., *Eur. J. Biochem.* 82:54–549 (1978). Assuming a flat polymer surface, the surface coverage of a monolayer of HRP is 2.7 ng HRP per $mm^2$.

In control experiments, polymer films not spin-coated with PFPA were similarly baked, irradiated, and incubated with HRP solution. The resulting films showed no HRP activity.

EXAMPLE 3

In this Example, we performed surface modification of the conducting polymer, poly(3-octylthiophene) (P3OT), Cai et al, *J. Mol. Electron.* 7:63–68 (1991), in a manner similar to the methodology described in Examples 1 and 2. The extent of immobilization of HRP on PFPA-NHS-modified P3OT films was 0.2±0.1 $ng/mm^2$ with film 3a (Scheme 10) and 0.3±0.1 $ng/mm^2$ with film 3b.

EXAMPLE 4

In this Example, we performed surface modification of a PS surface using PFPAs in combination with photolithography to generate micron-size patterns on the surface of the polymer. Compounds are as shown in Scheme 10.

A PS film was spin-coated with a nitromethane solution of 1a, baked as described above, and irradiated through a high-resolution photomask having a minimum feature size of 0.5 μm. Photolysis was carried out in a KSM Karl Suss deep-UV contact aligner. The film was then dipped in nitromethane for 20 seconds, air dried, and allowed to react with a solution of 5-(aminoacetamido)fluorescein (Molecular Probes, Inc., Eugene, Oregon) in ethanol (4 mg/mL) at 25° C. for 1 hour followed by thorough rinsing with ethanol.

FIG. 1 shows the resulting micron-size patterns as observed under a fluorescence microscope, further demonstrating this new surface modification strategy. The smallest features (0.5 μm) are resolved but are slightly broadened, probably owing to diffraction effects.

As a control, a PS film without spin-coating NHS active ester 1a was photolyzed, developed and treated with 5-(aminoacetamino) fluorescein. No fluorescent patterns were observed under the fluorescence microscope (data not shown).

EXAMPLE 5

In this Example we modified the surface of a preformed polymer microstructure. Compounds are as shown in Scheme 10.

A micron-scale pattern of PS, which had previously been fabricated on a silicon wafer using deep-UV lithography, was dipped in a nitromethane solution of 1a for 10 seconds, baked, and photolyzed as described above. The sample was then immersed in a solution of N-(5-aminopentyl) biotinamide (Molecular Probes, Inc., Eugene, Oreg.) in DMF (1 mg/0.2 mL) for 4 h, and washed with DMF followed by ethanol. Taking advantage of the strong affinity of avidin for biotin (Green, *Adv. Protein Chem.* 29:85–133 (1975); Heitzmann et al., *Proc. Nat. Acad. Sci. USA* 71:3537–3541 (1974)), fluorescein-avidin (Molecular Probes, Inc., Eugene, Oreg.) was attached to the surface by incubating the wafer in a solution of the fluorescent protein in pH 8.2 buffer (3.2 mg/0.5 mL) for 4 h.

Figure 2A:
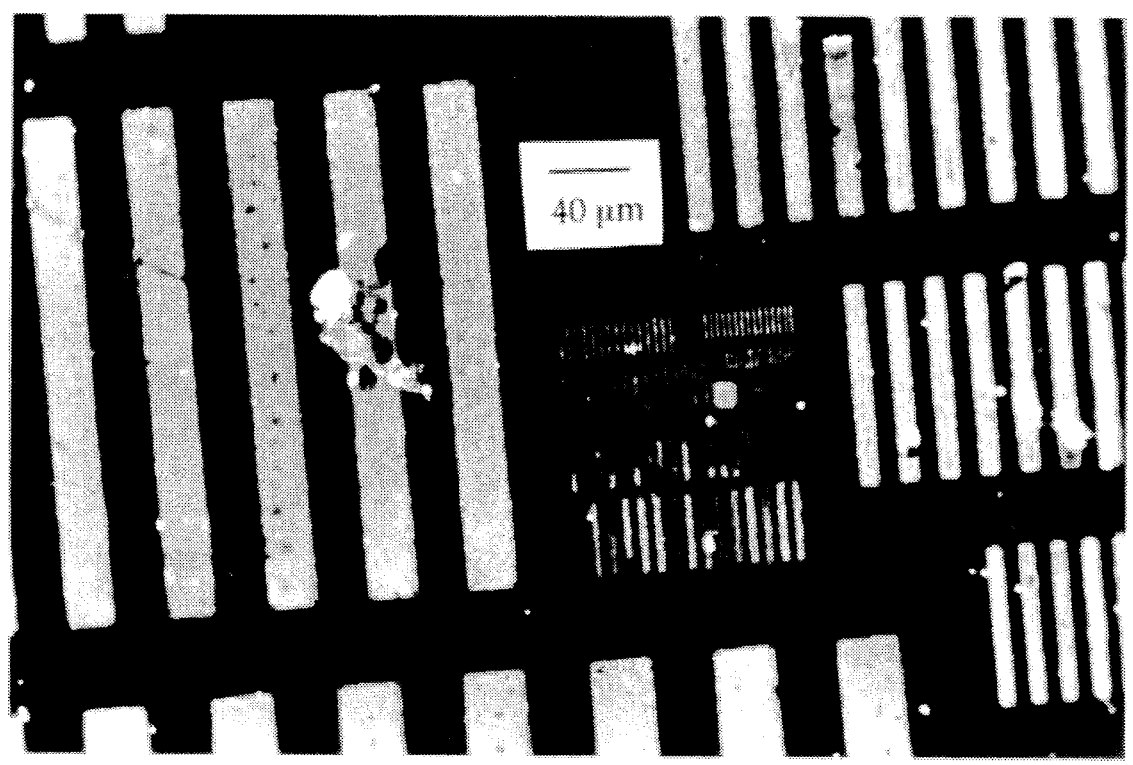
FIG. 2A is a photomicrograph of fluorescent protein formed by treating preformed polystyrene patterns with a PFPA compound (compound 1a in Scheme 1) followed by photolysis, then treating with N-(5-aminopentyl)biotinamide followed by fluorescein-avidin, as described in Example 5.
Figure 2B:
FIG. 2B is a photomicrograph of an experimental control wherein polystyrene patterns were treated with fluorescein-avidin only, as described in Example 5.

The resulting micron-size patterns are shown in FIG. 2A and the experimental control is shown in FIG. 2B. These results indicate that the biotin-avidin-fluorescein assembly became covalently attached to the preformed PS microstructure.

EXAMPLE 6

In this Example, we functionalized the surface of graphite. A piece of pyrolytic graphite was freshly cleaved using transparent adhesive tape and coated with a solution of 0.5% w/w N-hydroxysuccinimidyl 4-azidotetrafluorobenzoate (NHS-PFPA) in dry nitromethane by spinning at a speed of 1000 rpm. The coated graphite was baked at 60° C. for 20 minutes and irradiated for 5 minutes using 254-nm lamps at ambient temperature under air. The graphite was then incubated in a 50-μM solution of horseradish peroxidase (HRP) in $NaHCO_3$ buffer (pH 8.2) at 25° C. for 3 hours and rinsed thoroughly with phosphate buffer (pH 7.0).

The enzymatic activity of the functionalized graphite was determined spectroscopically at 420 nm and 25° C. in phosphate buffer using 2,2'-azino-bis(3-ethylbenzthiazoline-6-sulfonic acid) diammonium salt (ABTS) and hydrogen peroxide (1.8 mM ABTS/0.8 mM $H_2O_2$). Assuming that the immobilized HRP had the same activity as the native HRP, the extent of immobilization of HRP was 2.1 $ng/mm^2$.

A control experiment was performed as follows: A piece of freshly cleaved graphite was similarly baked, irradiated, and incubated with HRP solution. The enzyme-activity of the control was determined to be 0.4 ng $HRP/mm^2$. Thus, the control was not treated with NHS-PFPA.

Samples and controls were examined using atomic-force microscopy (AFM). The atomic-force microscope was operated in air at ambient temperature.

Figure 3A:
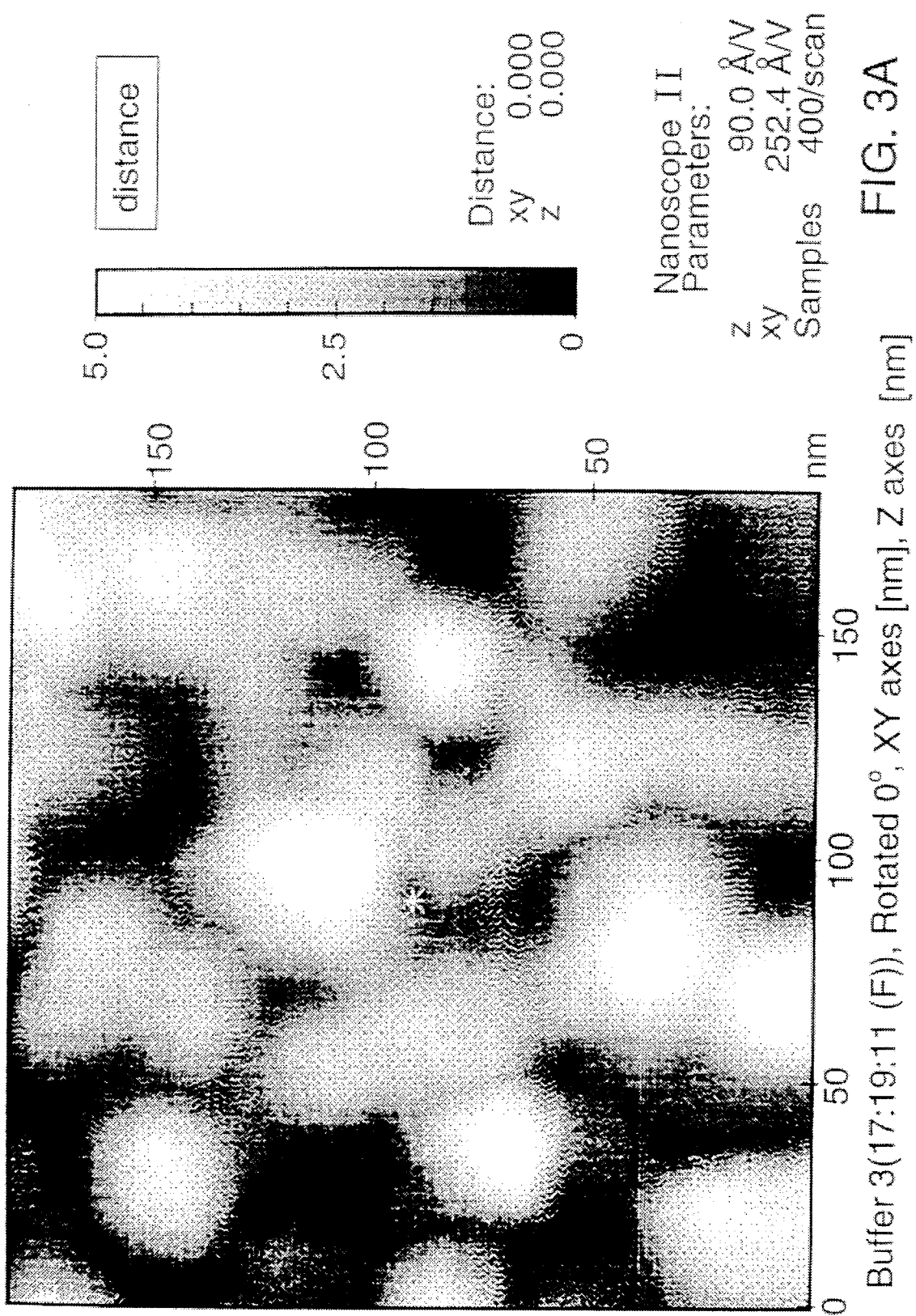
FIG. 3A is an image obtained with an atomic-force microscope of a freshly cleaved graphite surface functionalized first with NHS-PFPA, then with horseradish peroxidase, as described in Example 6.
Figure 3B:
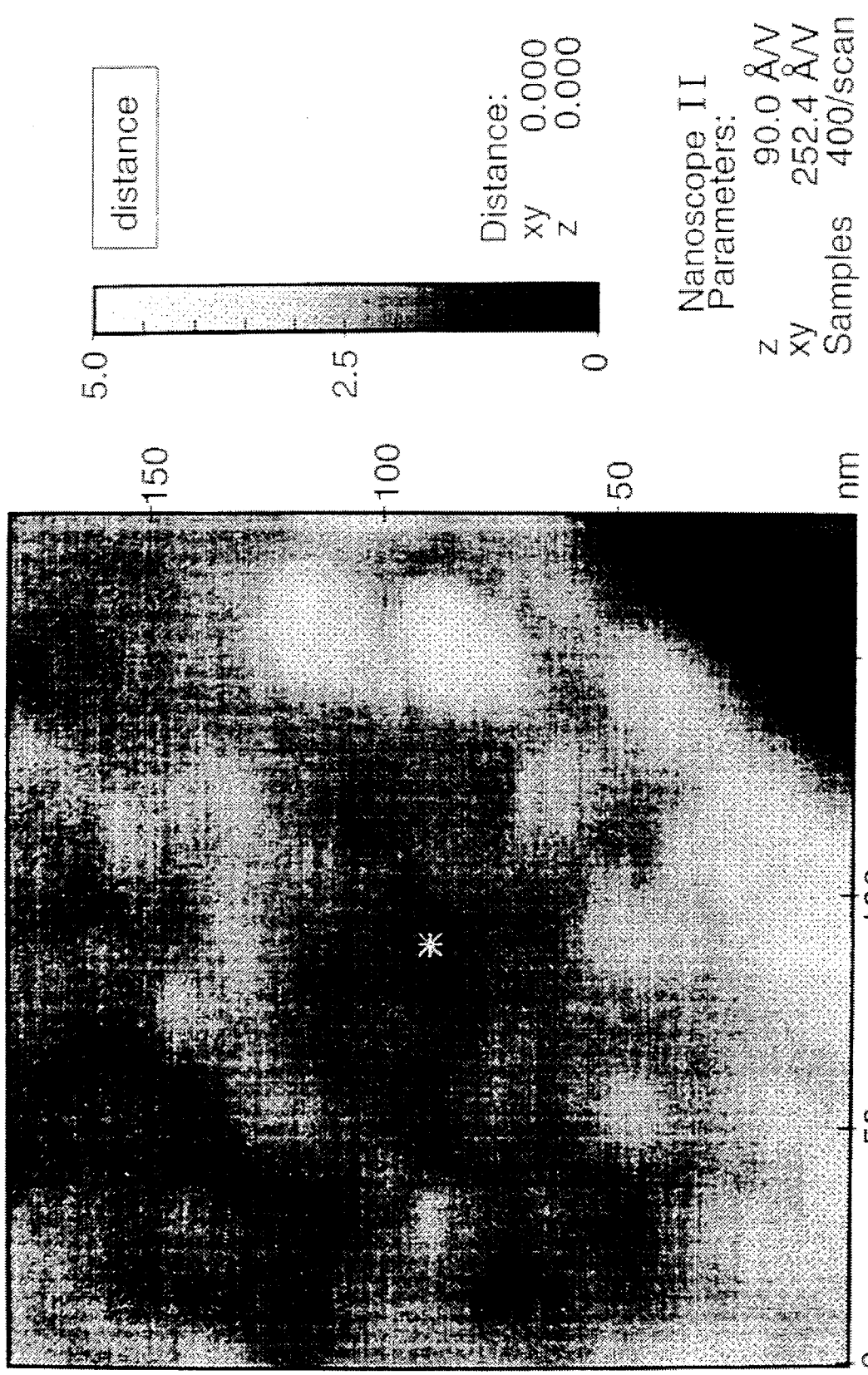
FIG. 3B is an atomic-force microscope image of an experimental control wherein a freshly cleaved graphite surface was treated with horseradish peroxidase but not with NHS-PFPA, as described in Example 6.

A representative AFM image of the sample is shown in FIG. 3A and of the control in FIG. 3B. In FIG. 3A, bright spheres correspond to immobilized HRP molecules. In FIG. 3B, only a few faint spheres were seen, indicating much less immobilization of the HRP molecules to the control surface.

Therefore, the NHS-PFPA is necessary to achieve substantial covalent attachment of HRP to the graphite surface.

EXAMPLE 7

The chemistry of this Example is illustrated in Scheme 11, wherein two photoactive biotins, PFPA-biotins 3 and 5 were prepared. These photoactive biotins could be used to functionalize a polymer surface with biotin groups. Such biotinylated surfaces can be further reacted so as to attach biomolecules to the substrate through biotin-binding proteins such as avidin.

Scheme 11

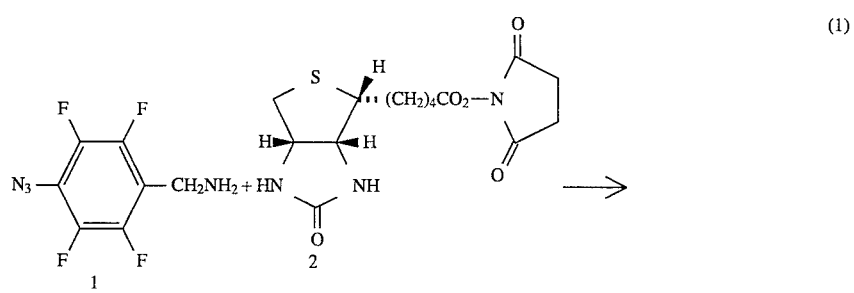

(1)

-continued
Scheme 11

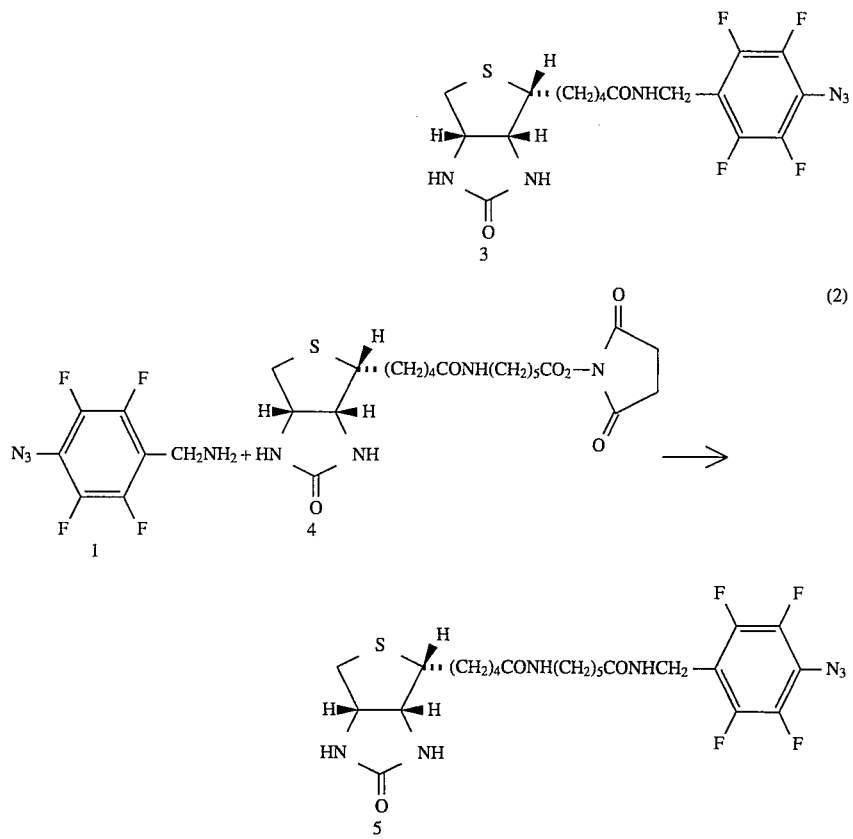

Synthesis of N-4-azido-2,3,5,6-tetrafluorobenzyl biotinamide (3) was performed as follows: To a solution of 33 mg (0.097 mmol) N-succinimidyl-D-biotin in 0.5 mL of DMSO-$d_6$ was added 27 mg (0.12 mmol) of 4-azido-2,3,5,6-tetrafluorobenzylamine. The resulting solution was maintained at room temperature for 0.5 hours, after which NMR revealed completion of the reaction. The solution was added dropwise into 10 mL water to form a precipitate. The precipitate was filtered, washed with water, and dried to yield 36.8 mg (85%) of 3 as an almost colorless solid having a mp=164°–165° C. $^1$H-NMR (CDCl$_3$+DMSO)-$d_6$): 1.157 (q,2), 1.40 (m,4), 1,950 (t,2), 2.87 (m,2), 4.01 (m,1), 4,20 (m,3), 5.41 (m,2), 7.53 (m,1). IR (KBr): 3454, 3290, 2931, 2161, 2125, 1704, 1654, 1549, 1493, 1420, 1239, 1054 cm$^{-1}$.

Synthesis of N-4-azido-2,3,5,6-tetrafluorobenzyl-6-(biotinamido)hexanamide (5) was performed as follows: To a solution of 49.2 mg (0.108 mmol) of N-succinimidyl-6-(biotinamido)hexanoate in 0.6 mL of dry DMF was added 32 mg (0.14 mmol) of 4-azido-2,3,5,6-tetrafluorobenzylamine. The solution was stirred at room temperature for one hour, then added dropwise into 10 mL water. The resulting precipitate was filtered, washed by water, and dried to yield 60.1 mg (99%) of 5 as a colorless solid with mp=160°–161° C. $^1$H-NMR (CDCl$_3$+DMSO-$d_6$): 0.98 (m,2), 1.14 (m,4), 1.31 (m,6), 1.85 (m,4), 2.4–2.5 (m,2), 2.8 (m,3), 3.92 (m,1), 4.10 (m,3), 5.52 (s,1), 5.56 (s,1), 6.76 (m,1), 7.56 (m,1). IR (KBr): 3438, 3301, 2935, 2162, 2177, 1700, 1652, 1547, 1499, 1416, 1239, 1054 cm$^{-1}$.

EXAMPLE 8

This Example pertains to the synthesis of several PFPA-based cross-linkers capable of functionalizing polymers. In particular, a group of NHS-ester functionalized PFPAs with different linker lengths between the NHS ester group and the PFPA group were synthesized. These functionalized PFPAs were particularly adapted for photo-cross-linking amino groups in biopolymers to proximally located chemical groups and for functionalization of polymers in general. The overall chemistry is diagrammed in Scheme 12.

Scheme 12

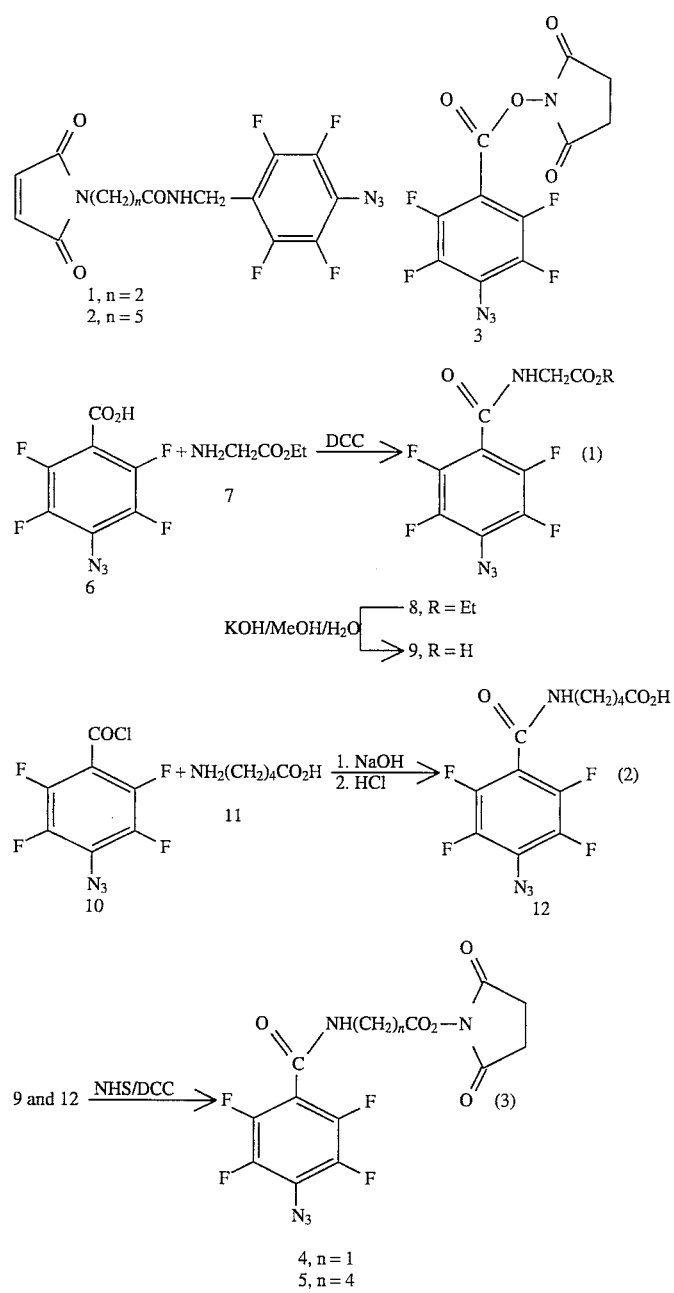

The chemistry utilizes maleimide-containing PFPAs 1 and 2 which were previously used to map cysteine residues introduced into ATPase by mutation, yielding a photo-crosslinking yield as high as 50 percent. Aggeler et al., *Biochemistry* 31:2956–2961 (1992).

The NHS-containing PFPAs 4 and 5 are particularly adapted for cross-linking of an amino group in a polypeptide chain to a proximally located chemical group by means of a photochemical —CH or —NH insertion reaction. These PFPAs can also be used to modify polymers with the NHS groups which can then be reacted with amino-containing reagents for introducing other functional groups into the polymers.

In Scheme 12, reaction of acid 6 and the glycine ethyl ester 7 with dicyclohexylcarbodiimide (DCC) as coupling reagent produced the amide 8 as follows: A mixture of 217 mg (1.55 mmol) of glycine ethyl ester hydrochloride and 158 mg (1.56 mmol) of triethylamine in tetrahydrofuran (7 mL) was stirred for 20 minutes. Afterward, 369 mg (1.57 mmol) of 4-azido-2,3,5,6 tetrafluorobenzoyl acid 6 and 324 mg DCC was added. The mixture was stirred overnight and filtered. The filtrate was evaporated and the residue dissolved in 20 mL of ethyl acetate. The solution was then dried and filtered. The filtrate was washed with 0.1 N HCl (2×10 mL), 5% $NaHCO_3$ (2×10 mL), and water (2×10 mL). The solution was dried and evaporated to yield a solid that was purified by preparative TLC to yield 160 mg (32% yield) of 8 as a colorless solid with a mp=85°–86° C. $^1H$ NMR: 1.321 (t,3, J=7.13), 4.239 (d,2, J=4.82), 4,273 (q,2, J=7.13), 6.540 (mb,1). IR: 2128, 1744, 1686, 1649, 1523, 1488, 1225, 1001 cm$^{-1}$. Anal. calcd for C$_{11}$H$_8$F$_4$N$_4$O$_3$: C, 41.26; H, 2.52; N, 17.50. Found: C, 41.46; H, 2.37; N, 17.66.

Subsequent hydrolysis produced the acid 9 as a solid in 31% overall yield, as follows: To a solution of 60 mg of 8 in 0.5 mL methanol was added 0.4 mL of a solution of 2.5% aqueous NaOH. The resulting solution was stirred for one hour. The solution was then acidified to pH<1 using 2N HCl. The precipitate was filtered and dried to yield 23 mg of 9 as a white solid. The filtrate was extracted by THF/CHCl$_3$ (1:1, 3×3 mL) and the extract was dried and evaporated to yield a further amount (32 mg) of 9 as a white solid (combined yield 55 mg, 99%) with a melting point of 147°–148° C. $^1$H-NMR (CDCl$_3$+DMSO-d$_6$): 4.339 (d,2, J=4.80), 6.527 (m,1) MS: 292 (2, M$^+$), 264 (20, M$^+$-N$_2$), 190 (20 NC$_6$F$_4$CO), 162 (100 NC$_6$F$_4$).

Reaction of the acyl chloride 10 with 5-aminopentanoic acid 11 under basic conditions followed by acidification produced the acid 12, as follows: To a solution of 238 mg (2.03 mmol) of 5-aminopentanoic acid 11 in 50% aqueous NaOH (0.4 mL) and 2.6 mL water was added 239 mg (0.942 mmol) of 4-azido-2,3,5,6-tetrafluorobenzoyl chloride 10. A precipitate was observed immediately. The mixture was stirred for 5 min and diluted with 3 mL water. The mixture was then stirred for another 15 minutes and acidified to pH<1 using 2-N HCl. The precipitate was filtered and washed with 0.1 N HCl (1 mL) and 2 mL water, and dried to yield 231 mg of solid. The solid was washed using 1 mL ether and crystallized in a mixture of tetrahydrofuran and ether to yield 171 mg (54% yield) of 12 as a colorless solid with mp=160°–161° C. $^1$H-NMR (CDCl$_3$+DMSO-d$_6$): 1.753 (m,4), 2.540 (t,2, J=6.73), 3.504 (q,2, J=5.90), 6.1 (m,1). MS: 334 (5, M$^+$), 317 (4, M$^+$—OH), 306 (40, M$^+$—N$_2$), 190 (15 NC$_6$F$_4$CO), 162 (100, NC$_6$F$_4$). High-resolution MS calc'd for C$_{12}$H$_{10}$F$_4$N$_4$O$_3$: 34.0687; found: 334.0710.

The NHS-active esters 4 and 5 were prepared by reaction of acids 9 and 12 with N-hydroxysuccinimide in the presence of DCC, respectively. In particular, to prepare 4, a solution of 39.3 mg (0.134 mmol) of 9, 29.3 mg (0.142 mmol) of DCC, and 16.6 mg of NHS in 0.5 mL THF was stirred at 25° C. overnight. The resulting mixture was filtered. The filtrate was evaporated to yield a solid that was redissolved in 1 mL CH$_2$Cl$_2$. The resulting mixture was filtered. The filtrate was evaporated to yield 42 mg (80% yield) of 4 as a colorless solid. The analytical sample was obtained via recrystallization in acetone/hexane as a colorless solid having a mp=145°–146° C. $^1$H-NMR: 2.883 (s,4), 4,637 (d,2, J=5.40), 6.548 (mb,1). IR: 2129, 1792, 1748, 1718, 1699, 1649, 1520, 1489, 1204 cm$^{-1}$. MS: 389 (8, M$^+$), 275 (60 M$^+$-NHS), 247 (27, M$^+$-NHS-N$_2$), 218 (65, M$^+$-CONHS-N$_2$-H), 190 (45, NC$_6$F$_4$CO), 162 (100, NC$_6$F$_4$). High-resolution MS calculated for C$_{13}$H$_7$F$_4$N$_5$O$_5$: 389.0382; found: 389.0405.

NHS ester 5 was prepared from acid 12 in a manner similar to ester 4 and was isolated as a colorless solid at 91% yield having a mp=93°–95° C. $^1$H-NMR: 1.77 (m,2), 1.85 (m,2), 2.691 (t,2, J=6.65), 2.841 (s,4), 3.512 (q,2, J=6.24), 6.22 (m,1). IR: 2127, 1817, 1786, 1742, 1681, 1649, 1602, 1526, 1487, 1260, 1209, 1069 cm$^{-1}$. MS: 431 (5, M$^+$). 403 (3, M$^+$-N$_2$), 317 (22, M$^+$-NHS), 289 (8, M$^+$-NHS-N$_2$), 162 (100, NC$_6$F$_4$). High-resolution MS calcd for C$_{16}$H$_{13}$F$_4$N$_5$O$_5$: 431.0850; found: 431.0866.

The two NHS-active esters 4 and 5, together with NHS-active ester 3, formed a group of NHS-containing PFPAs having linkers of different lengths between the PFPA and the NHS groups. Thus, compounds 3, 4, and 5 are useful for functionalizing amino groups in biopolymers such as polypeptide chains via the NHS group and subsequent cross-linking to a proximally located biopolymer by photo-generated nitrene intermediates. The compounds can also be used for functionalizing substrates, including polymeric substrates.

EXAMPLE 9

This Example is similar to Example 8, except that two heterobifunctional and cleavable PFPA-based crosslinkers were synthesized, as shown generally by the formula:

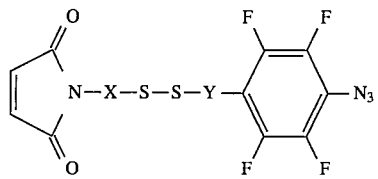

For example, the following compound was synthesized:

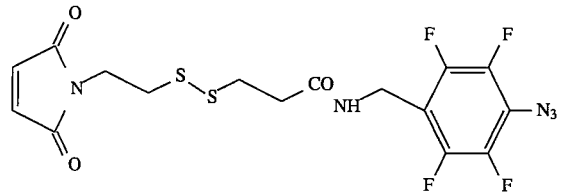

In general, the PFPA portion of the molecule can be used to functionalize a substrate, allowing the maleimide portion to be used for attaching another functional group (via reaction with an SH— containing molecule or a 1,3-diene-containing molecule in a Diels-Alder type reaction.) Then, at a later time, the maleimide side can be cleaved from the surface under mild conditions. Another cleavable group can be a 1,2-diol linkage cleavable using periodic acid.

EXAMPLE 10

This Example pertains to the functionalization of polystyrene.

A 1-cm$^2$ piece of silicon wafer was coated with a solution of 5% w/w polystyrene by spinning at 1000 rpm. The wafer was then spin-coated with a solution of 0.5% w/w of N-hydroxysuccinimidyl-4-azido-2,3,5,6-tetrafluorobenzoate in nitromethane at a speed of 1000 rpm, baked at 60° C. for 20 minutes, and subjected to electron-beam lithography. The coated wafer was dipped in nitromethane for 20 seconds to remove any unattached PFPA, air dried, and allowed to react with a solution of 2 mg/mL 5-(aminoacetamido)fluorescein in ethanol at 25° C. for 1 hour. The wafer was then immersed in ethanol overnight to remove the non-covalently attached fluorescein residues.

Figure 4A:
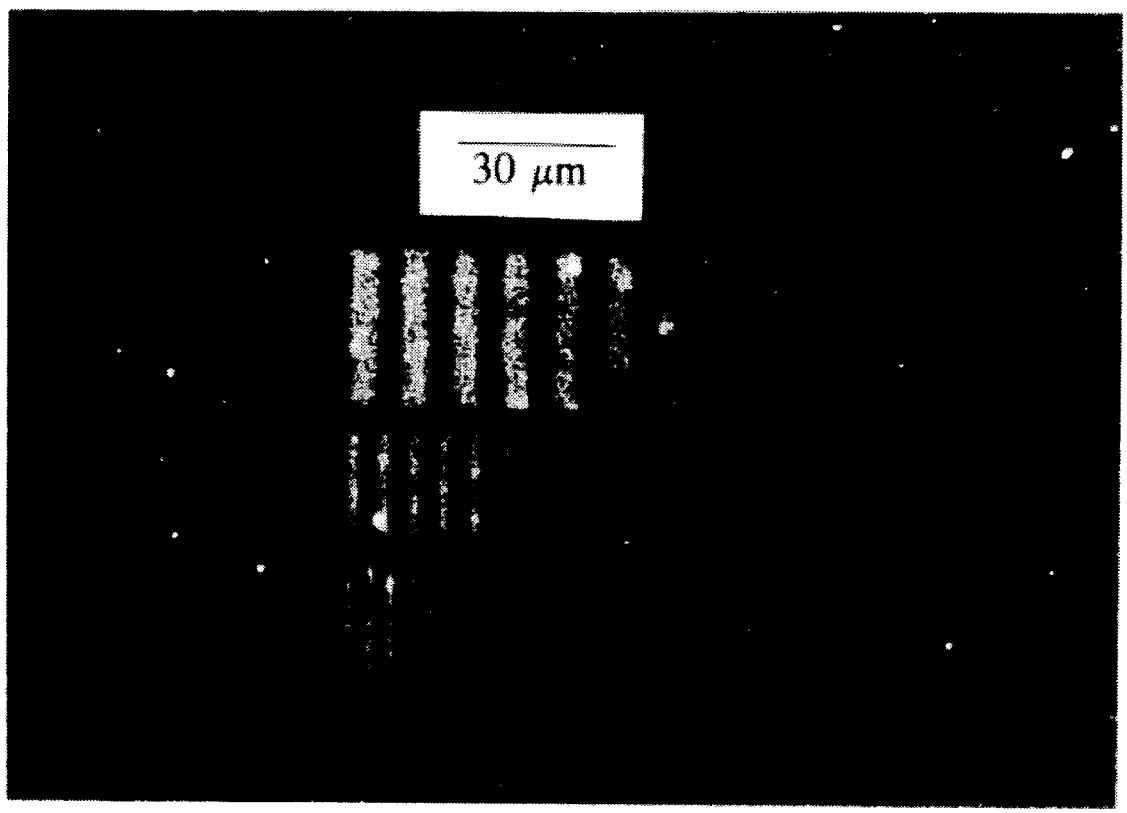
FIG. 4A is a photomicrograph obtained using a fluorescence microscope 450–490 excitation wavelength; >510 nm emission wavelength) of a polystyrene surface functionalized with NHS-PFPA using an electron beam as a reaction-energy source, as described in Example 10.

The results are shown in FIG. 4A (legend in FIG. 4B), depicting patterns observed under a fluorescence microscope 450–490 excitation, >510 nm emission). The patterns were delineated by electron-beam lithography with the line widths of (from thickest to thinnest): 5 µm, 2 µm, 1 µm, 0.5 µm, 0.2 µm, and 0.1 µm (FIG. 4B). As shown in FIG. 4B, the dosages are 40, 35, 30, 25, 20, 15, 10, 5, and 1 µC/cm$^2$ from left to right for the 5, 2, and 1 µm widths and from right to left for the 0.5, 0.2, and 0.1 µm widths.

In FIG. 4A, features of 0.2 µm were resolved. The smallest features (0.1 µm) were not resolved in this unoptimized experiment. The sensitivity is about 10 to about 30 µC/cm².

While the invention has been described in connection with preferred embodiments and multiple examples, it will be understood that it is not limited to those embodiments. On the contrary, it is intended to cover all alternatives, modifications, and equivalents as may be included within the spirit and scope of the invention as defined by the appended claims.

What is claimed is:

1. A method for producing a functionalized surface on a substance, comprising the steps:
   (a) providing a non-fluid substrate having a surface comprising surface molecules having chemical moieties each capable of undergoing an addition reaction with a nitrene;
   (b) providing a first functionalizing reagent comprising molecules each having a nitrenogenic group and a first functional group, the first functionalizing reagent being selected from the group consisting of functionalized perfluorophenyl azides having the structure:

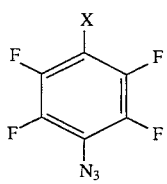

wherein X is selected from the group consisting of CN; CONH₂; CHO; CO₂CH₃; COCH₃; NO₂; CO₂H; COCl; CO-imidazole; CONHS; CH₂OH; CH₂NH₂; COCH₂Br; N-maleimido; NH-biotinyl; CONH—R, wherein R is a polypeptide; CONH—X—S—S—Y—NH-biotinyl, wherein X and Y are spacer atoms; and CONHS—SO₃Na;
   (c) applying the first functionalizing reagent to the substrate surface; and
   (d) either subsequent to or simultaneously with step (c), exposing preselected regions on the substrate surface to a reaction-energy source so as to convert the nitrenogenic groups, on molecules of the first functionalizing reagent on the surface, to nitrenes that undergo addition reactions with the chemical moieties on the surface molecules, thereby covalently bonding the first functional groups to the surface molecules to create a pattern of functionalized surface regions relative to non-functionalized regions.

2. A method as recited in claim 1 wherein step (a) comprises providing a substrate having surface molecules possessing chemical moieties selected from a group consisting of —CH, —NH, —OH, —C—C—, —C═C—, SiO—H, Si—OH, and Si—OSi moieties.

3. A method as recited in claim 1 wherein step (a) comprises providing a substrate selected from a group consisting of polymeric materials, siliceous materials, semiconducting materials, metals, and allotrophic forms of elemental carbon.

4. A method as recited in claim 1 wherein, in step (c), the reaction-energy source is selected from a group consisting of energized electrons, energized ions, photons, and heat.

5. A method as recited in claim 1 wherein exposing preselected regions on the substrate surface to the reaction-energy source is performed by applying a photomask to the substrate surface, the photomask thereby defining a preselected pattern on the surface of regions exposable to the reaction-energy source and other regions not exposable to the reaction-energy source; then exposing the surface to the reaction-energy source in a manner such that the photomask is situated between the reaction-energy source and the substrate surface.

6. A method as recited in claim 1 wherein the reaction-energy source comprises photons.

7. A method as recited in claim 1 wherein exposing preselected regions on the substrate surface to the reaction-energy source is performed by impinging a beam of energized electrons on preselected regions on the substrate surface.

8. A method as recited in claim 1 wherein, in step (b), the first functionalizing reagent is selected from a group consisting of perfluorophenyl azides derived from 4-azido-2,3,5,6-tetrafluorobenzoic acid.

9. A method as recited in claim 8 wherein, in step (b), the first functionalizing reagent is selected from a group consisting of N-hydroxysuccinimide-functionalized perfluorophenyl azides.

10. A method as recited in claim 1 wherein, in step (b), the first functional group on molecules of the first functionalizing reagent is selected from a group consisting of carboxyl groups, acid halides, acyl imidazoles, thioesters, p-nitrophenyl esters, alkyl esters, alkenyl esters, alkynyl esters, aromatic esters, amides, free alcohol groups, alcohol groups esterified to a carboxylic acid, haloalkyl groups, maleimido and other dienophilic groups, aldehydes, ketones, and sulfonyl halide groups.

11. A method as recited in claim 1 wherein step (a) comprises providing a hydrophobic substrate and wherein the first functional group is less hydrophobic than the substrate.

12. A method as recited in claim 1 wherein step (a) comprises providing a hydrophilic substrate and wherein the first functional group is less hydrophilic than the substrate.

13. A method as recited in claim 1 further comprising, after step (d), the steps:
   providing a second functionalizing reagent comprising molecules each having a second functional group reactive with the first functional group;
   exposing the first functional groups bonded to the substrate surface to the second functionalizing reagent under conditions conducive for causing the second functional groups to undergo chemical reactions with the first functional groups, thereby covalent bonding molecules of the second functionalizing reagent to the substrate surface.

14. A method as recited in claim 13 wherein the first functional group is an ester and the second functional group is selected from a group consisting of hydroxyls, primary amines, and secondary amines.

15. A method as recited in claim 13 wherein the molecules of the second functionalizing reagent each further comprise a third functional group.

16. A method as recited in claim 15 wherein the third functional group comprises a polypeptide.

17. A method as recited in claim 15 wherein the third functional group comprises a nucleic acid.

18. A method as recited in claim 15 wherein the third functional group comprises a polysaccharide.

19. A method as recited in claim 15 wherein the third functional group comprises a moiety selected from a group consisting of hydrophilic, hydrophobic, surface-active, carcinogenic, mutagenic, diagnostic, therapeutic, fluorescent, and radiolabeled moieties.

20. A method for producing a functionalized surface on a substance, comprising the steps:

(a) providing a non-fluid substrate having a surface comprising surface molecules having chemical moieties each capable of undergoing an addition reaction with a nitrene;

(b) providing a first functionalizing reagent comprising molecules each having a nitrenogenic group and a first functional group;

(c) providing a second functionalizing reagent comprising molecules each having a second functional group reactive with the first functional group;

(d) adding the first functionalizing reagent to the second functionalizing reagent under conditions conducive for an addition reaction of the first functional group with the second functional group so as to cause molecules of the second functionalizing reagent to bond to molecules of the first functionalizing reagent, thereby forming a reaction product of molecules each comprising a molecule of the first functionalizing reagent bonded to a molecule of the second functionalizing reagent;

(e) applying molecules of the reaction product to the substrate surface;

(f) either subsequent to or simultaneously with step (e), exposing the surface to a reaction-energy source so as to convert the nitrenogenic groups, on molecules of the reaction product on the surface, to nitrenes that undergo addition reactions with the chemical moieties on the surface molecules, thereby covalently bonding molecules of the reaction product to the surface molecules.

21. A method for functionalizing a polymeric substrate, comprising the steps:

(a) providing a polymeric material comprised of polymer molecules possessing at least one reactive group selected from a group consisting of —NH, —CH, —OH, —C—C—, and —C═C— groups;

(b) applying an N-hydroxysuccinimide-functionalized perfluorophenyl azide to a surface of the substrate to produce an NHS-PFPA-coated surface of the substrate; and (c) exposing the NHS-PFPA-coated surface to a reaction-energy source so as to cause the N-hydroxysuccinimide-functionalized perfluorophenyl azide to undergo nitrene addition to the reactive groups on the polymer molecules.

22. A non-fluid substance having a surface functionalized according to the method recited in claim 21.

23. A non-fluid substance having a surface functionalized according to the method recited in claim 1.

24. A non-fluid substance having a surface functionalized according to the method recited in claim 20.

25. A method for functionalizing surface molecules of a substrate, comprising:

providing a substrate having chemical moieties each capable of undergoing an addition reaction with a nitrene;

providing a first functionalizing reagent from a group consisting of functionalized perfluorophenyl azides according to the formula

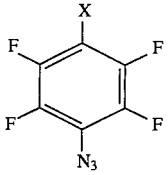

wherein X is selected from a group consisting of CN; $CONH_2$; CHO; $CO_2CH_3$; $COCH_3$; $NO_2$; $CO_2H$; COCl; CO-imidazole; CONHS; $CH_2OH$; $CH_2NH_2$; $COCH_2Br$; N-maleimido; NH-biotinyl; CONH—R, wherein R is a polypeptide; CONH—X—S—S—Y—NH-biotinyl, wherein X and Y are spacer atoms; and CONHS—$SO_3Na$;

bringing the first functionalizing reagent into reactive proximity to the substrate molecules; and while the substrate molecules and the first functionalizing reagent are in reactive proximity, exposing the substance to a particle beam to convert the nitrenogenic groups to nitrenes that undergo addition reactions with the chemical moieties on the polymer molecules, thereby covalently bonding the first functionalizing reagent to preselected portions of the polymer molecules.

26. The method according to claim 25 wherein the particle beam is an electron beam.

27. The method according to claim 25 wherein the particle beam is an ion beam.

28. The method according to claim 25 wherein the step of exposing comprises exposing the substrate to a particle beam in a preselected pattern, thereby covalently bonding the functionalizing reagent to the substance in portions of the substrate corresponding to the pattern.

29. A product produced according to the process of claim 25.

* * * * *